United States Patent [19]

Alpern et al.

[11] Patent Number: 5,350,060
[45] Date of Patent: Sep. 27, 1994

[54] PROCEDURE KIT AND PACKAGE

[75] Inventors: Marvin Alpern, Glen Ridge, N.J.; Robert Cerwin, Pipersville, Pa.

[73] Assignee: Ethicon, Inc., Somerville, N.J.

[21] Appl. No.: 6,005

[22] Filed: Jan. 15, 1993

[51] Int. Cl.$^5$ ............................................. B65D 85/24
[52] U.S. Cl. ................................... 206/63.3; 206/380
[58] Field of Search ...................... 206/63.3, 63.5, 227, 206/380, 383, 388, 389, 408, 409, 495

[56] References Cited

U.S. PATENT DOCUMENTS

| | | | |
|---|---|---|---|
| 4,391,365 | 7/1983 | Batchelor | 206/63.3 |
| 4,424,898 | 1/1984 | Thyen et al. | 206/380 |
| 4,869,367 | 9/1989 | Kawasaki et al. | 206/409 |
| 4,961,498 | 10/1990 | Kalinski et al. | |
| 4,967,902 | 11/1990 | Sobel et al. | 206/63.3 |
| 4,984,685 | 1/1991 | Douglas | 206/408 |
| 5,052,551 | 10/1991 | Cerwin et al. | 206/380 |
| 5,056,658 | 10/1991 | Sobel et al. | 206/380 |
| 5,099,994 | 3/1992 | Kalinski et al. | |
| 5,131,533 | 7/1992 | Alpern | |
| 5,165,217 | 11/1992 | Sobel et al. | |
| 5,179,818 | 1/1993 | Kalinski et al. | |
| 5,180,053 | 1/1993 | Cascio et al. | 206/63.3 |
| 5,213,210 | 5/1993 | Cascio et al. | 206/63.3 |
| 5,230,424 | 7/1993 | Alpern et al. | |

Primary Examiner—Jimmy G. Foster
Attorney, Agent, or Firm—Emil Richard Skula

[57] ABSTRACT

A package for a procedure kit that defines a suture winding channel and a surgical needle and suture procedure kit. The package may contain a variety of sizes and types and lengths of sutures and needles including at least one double-armed suture. The package has a base having a central area. An inner wall extends up from the base about the periphery of the central area. An outer wall also extends from the base. The outer wall and the inner wall form the channel. At least one spacer or separator member is located in the channel for separating the channel into at least two coplanar sections. A needle park means extends from the central area for receiving and holding surgical needles. The package and kit may be overwrapped with foil or paper and inserted into a conventional thermal plastic blister pack.

113 Claims, 9 Drawing Sheets

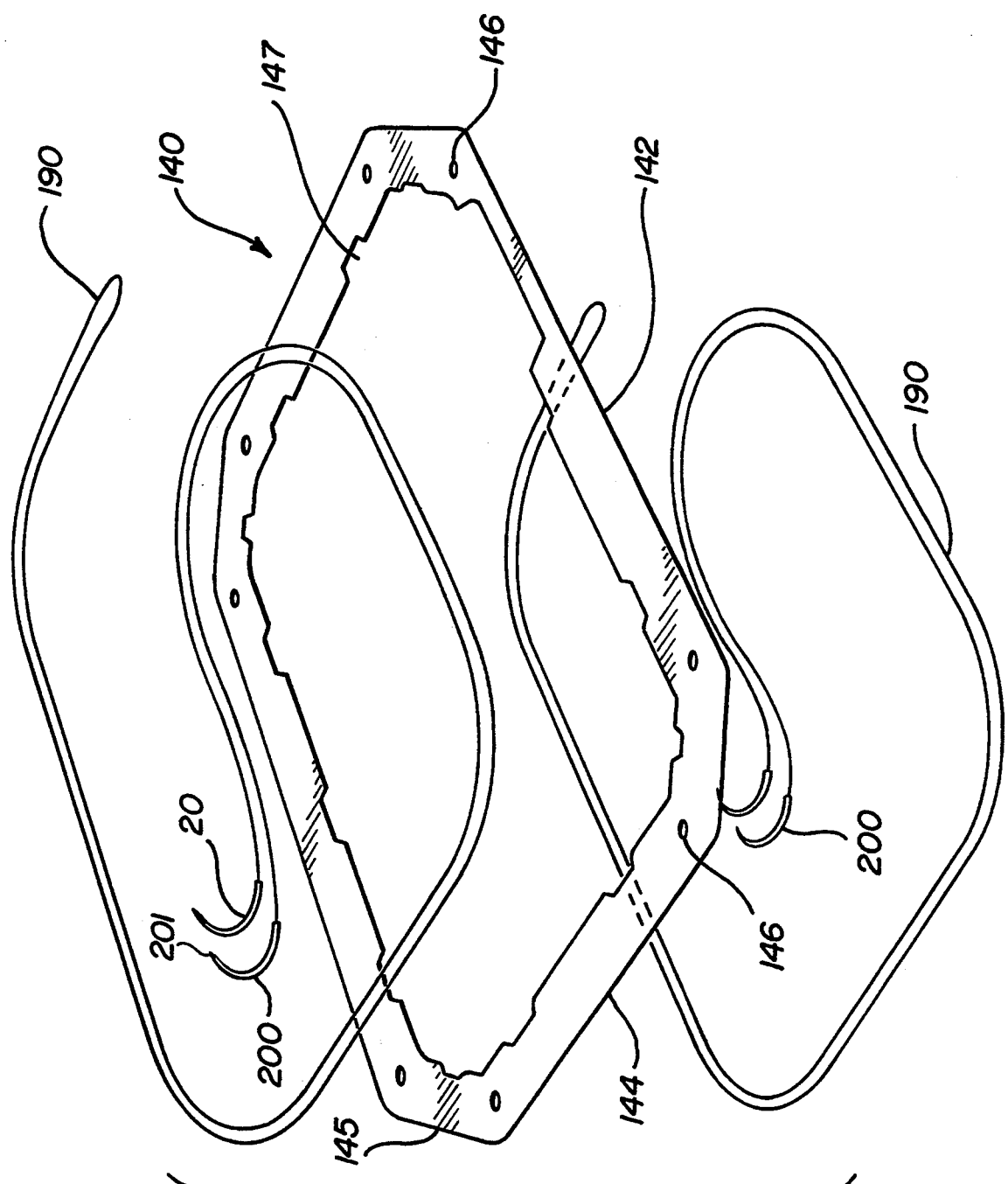

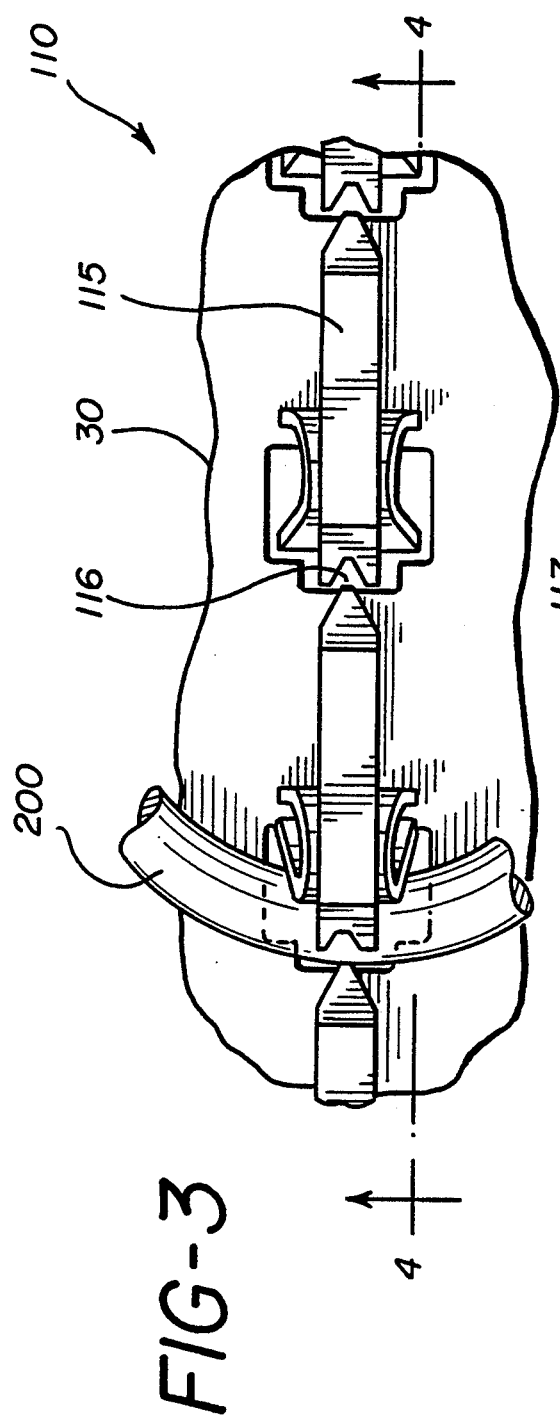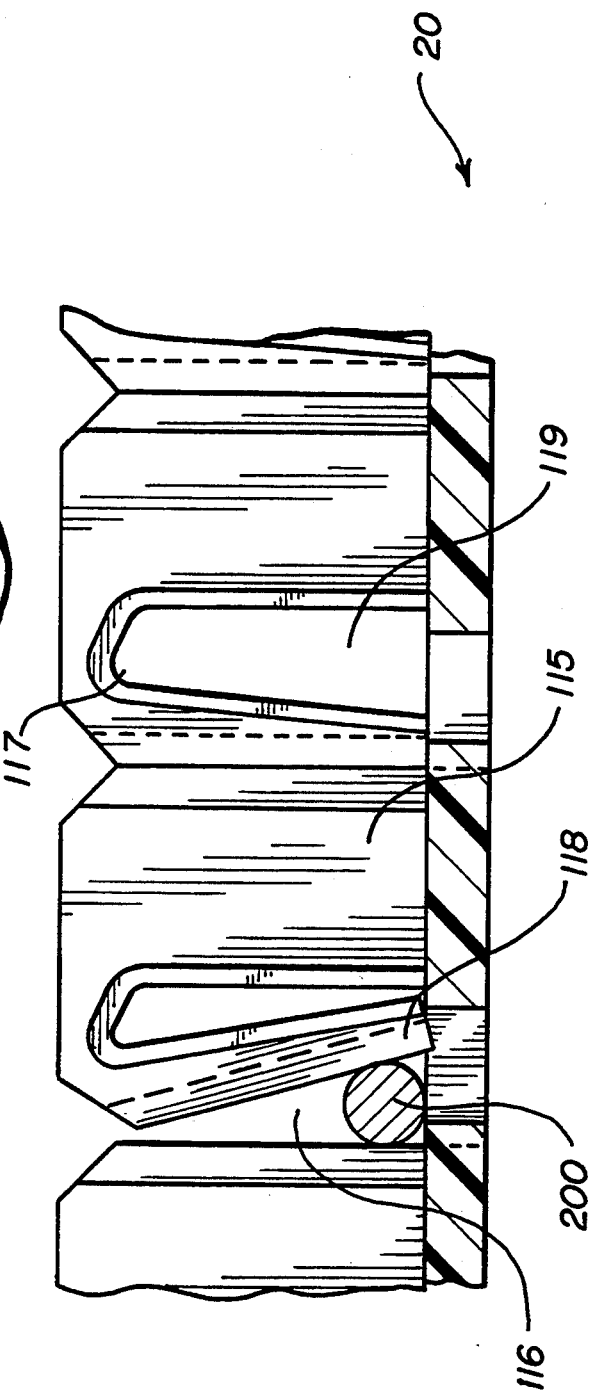

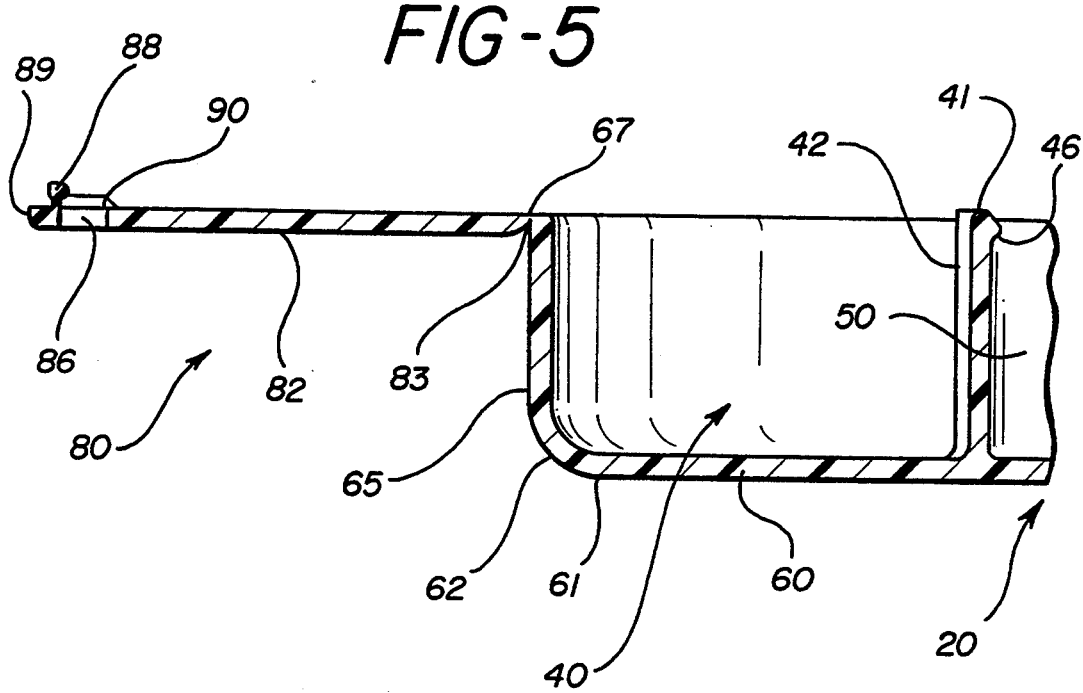
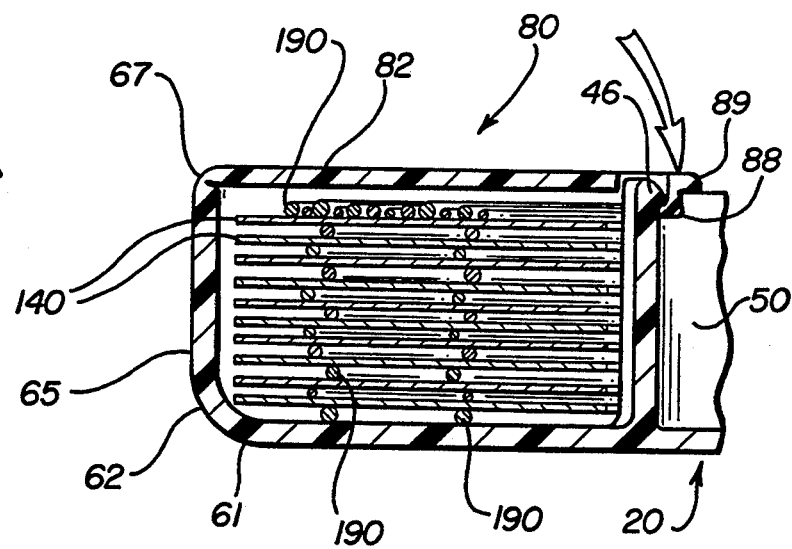

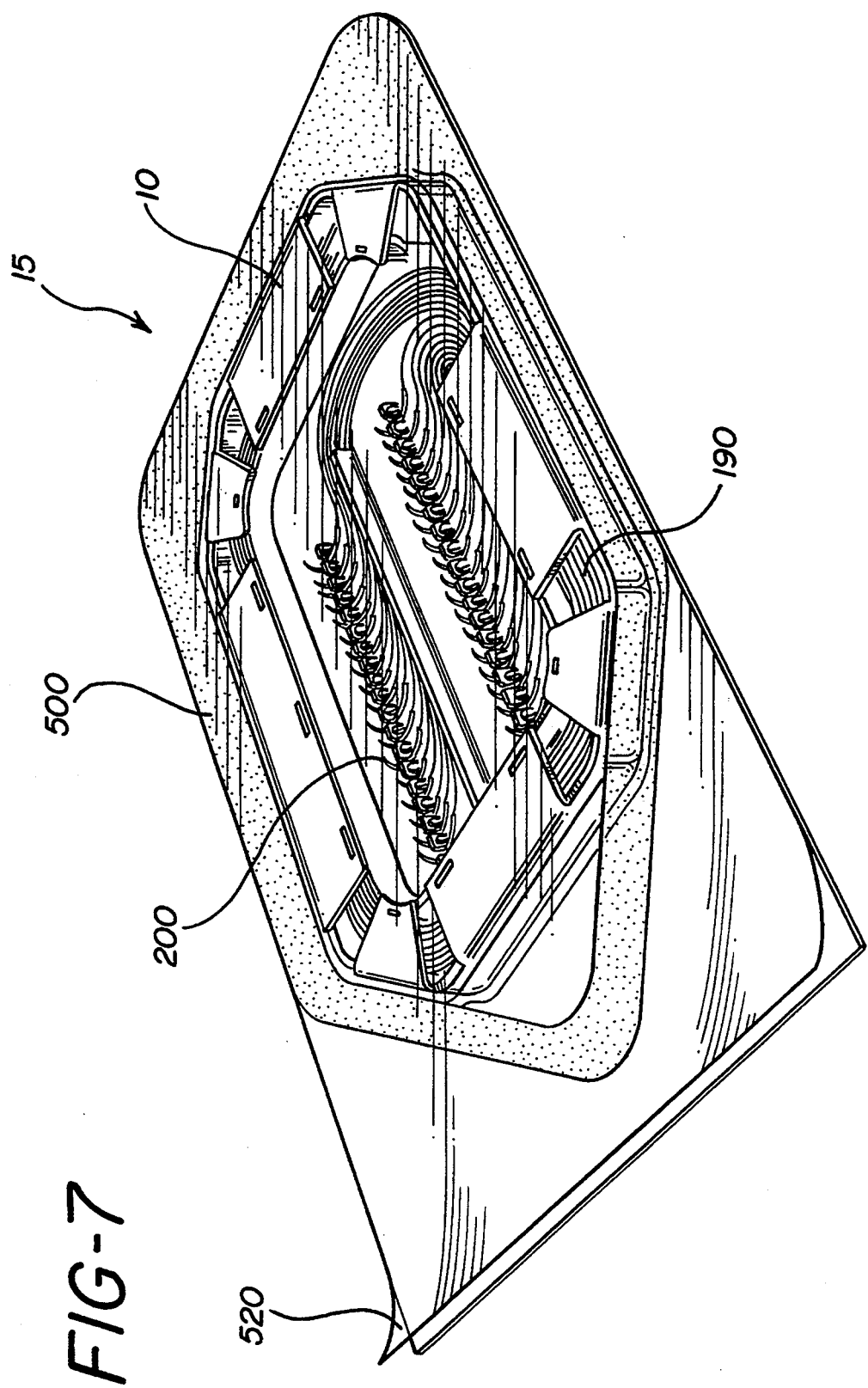

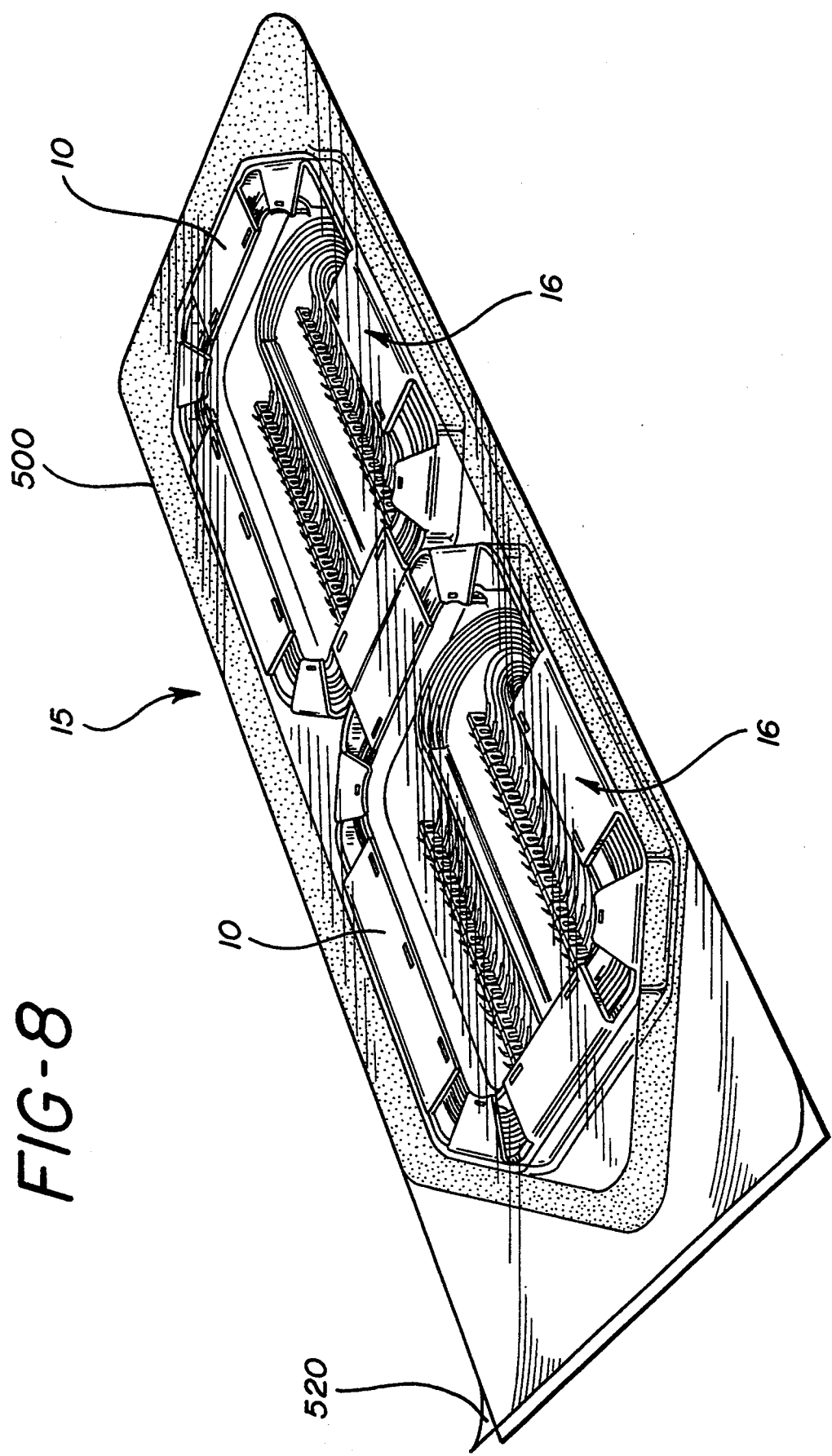

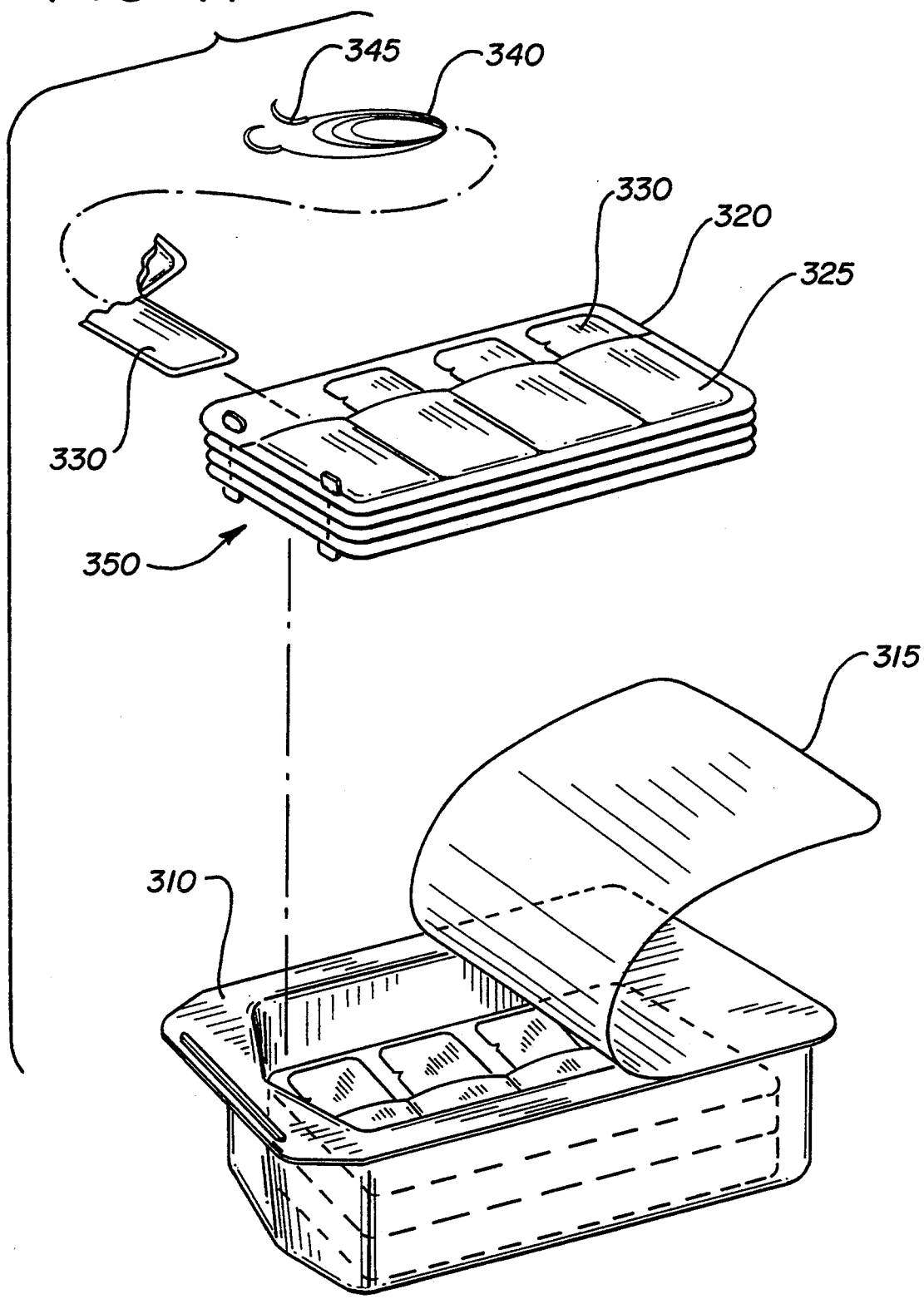

PROCEDURE KIT AND PACKAGE

FIELD OF THE INVENTION

The field of art to which this invention relates is kits and packages for kits, in particular, a surgical needle and suture procedure kit and a package for holding such a kit.

BACKGROUND ART

Surgical needles and sutures are typically packaged in single-use, disposable packages. The packages may consist of conventional packages such as foil packets, plastic trays, and paper folder packages. The sizes and types of packages used will vary in accordance with the particular sizes and types of surgical needles and sutures.

Commonly assigned, co-pending U.S. Pat. application Ser. No. 901,356 filed on Jun. 19, 1992 discloses a multi-strand suture package and cover latching element. The package includes a tray, a cover, a peripheral channel for sutures and an array of resilient cantilevered fingers to prevent sutures from lifting up out of the channel.

There are numerous types and sizes of surgical needles and sutures. Sutures may, for example, be single-armed wherein a single surgical needle has a single suture attached to it. Or, the sutures may be doubled-armed wherein each suture has a surgical needle mounted to both of its ends. It is also known to use sutures which are not armed with a needle. Conventional sutures may be monofilament or braided, and, either absorbable or nonabsorbable. In addition, conventional surgical needles may be curved or straight and may have taper points, cutting points or blunt points.

It is known that different types of needles and sutures are used for suturing different types of tissue within the body. In any given surgical procedure, numerous types and sizes of surgical needles and sutures will be utilized. The sizes and types of needles and sutures used during each stage of the procedure will depend upon the type and nature of the tissue which the surgeon is suturing, e.g., muscle, cutaneous, blood vessels, bone or organs.

Since the quantities, sizes and types of needles and sutures used for particular surgical procedures are well known, it is common for manufacturers to package procedure kits for particular surgical procedures, e.g., cardiovascular, gynecological, urological, etc. These kits typically consist of all of the sutures and needles needed for a particular surgical procedure individually packaged and arranged in a blister pack tray. The needles and sutures are typically individually packaged. When dealing with such a kit in the operating room, the scrub nurse must open each and every needle packet in such a kit and then dispose of the individual packaging as well as the kit packaging. Not only is this a time consuming job, since a kit may contain hundreds of needles and sutures, but it results in the generation of substantial amounts of waste packaging material that must be disposed of.

There is a need in this art for a package for a surgical procedure kit wherein various types and sizes of surgical needles and sutures can be collectively packaged within a single package. This would allow a scrub nurse to open up a single package rather than having to open up multiple, individual suture packages. Such a package would eliminate excess packaging material and also eliminate the need to dispose of such excess packaging material. Certain surgical procedures may require several packages containing subkits due to the quantity of needles and sutures needed, however this would still provide a major advantage in terms of eliminating the opening of numerous individual suture packages.

Therefore, it is an object of the present invention to provide a package for a surgical procedure kit wherein the kit contains surgical needles and sutures.

It is a further object of the present invention to provide a package for a surgical needle and suture procedure kit which would allow the packaging of various types and sizes of needles and sutures in one single package, including single-armed and double armed sutures.

It is still a further object of the present invention to provide a package for a procedure kit having minimal packaging materials.

It is yet another object of the present invention to provide a package for a procedure kit wherein all of the sutures and needles contained in the kit are accessible by opening either a single package or several subkit packages.

It is yet a further object of the present invention to provide a surgical procedure kit comprising a plurality of surgical needles and sutures packaged in a single package.

SUMMARY OF THE INVENTION

Accordingly, a package for a surgical procedure kit that defines a suture winding channel is disclosed. The package may be used for a procedure kit containing various types and sizes of sutures and needles, including single-armed and double-armed sutures. The package has a base having a central area. An inner wall extends up from the base about the periphery of the central area. Preferably, the inner wall comprises a pair of substantially opposed longitudinal and a pair of substantially opposed latitudinal walls. The ends of the latitudinal walls are preferably connected to the ends of the longitudinal walls. The suture package has an outer wall extending up from the base. The inner wall and the outer wall form a suture winding channel. At least one spacer or separator member is located in the channel for separating the channel into at least two coplanar sections. In a preferred embodiment, the longitudinal walls and the latitudinal walls are connected by curved intermediate wall sections. However, the inner wall may have a variety of geometric shapes including oval, round and polyhedral. Preferably, a needle park means is mounted to, or extends from, the central area for receiving and holding surgical needles.

Yet another aspect of the present invention is a procedure kit for a surgical procedure. The procedure kit comprises a plurality of surgical needles and sutures of various types and sizes wherein the surgical needles and sutures are packaged in the above-described package. Preferably, at least one of the sutures is a double-armed suture. However, the kit may consist of only single-armed and/or unarmed sutures.

Still yet another aspect of the present invention is a procedure kit for a surgical procedure wherein the kit consists of several subkits. The procedure kit comprises a plurality of surgical needles and sutures of various types and sizes wherein the surgical needles and sutures are packaged in the above-described packages to form subkits.

Yet another aspect of the present invention is a method of packaging a plurality of needles and sutures for a particular surgical procedure. The method comprises winding the needles and sutures in the suture winding channel of the above-described package. The method further comprises using the previously-mentioned separator members to separate each double-armed suture from other doubled-armed and single-armed sutures.

Other features and advantage of the invention will become more apparent from the following description and accompanying drawings.

BRIEF DESCRIPTION OF THE DRAWING

FIG. 1A is a perspective view of a separator member of the package of FIG.1 located between, and separating, coplanar double-armed sutures in a wound configuration.

FIG. 3 is an enlarged partial perspective view of a needle engaged in a needle park means of the package of the present invention.

FIG. 4 is an enlarged partial cross-section along view line 4—4 of the needle park means of FIG. 3.

FIG. 5 is an enlarged partial cross-section of the suture winding channel of the package of FIG. 2 taken along view line 5—5; the retaining door is shown in the open position.

FIG. 6 is a partial cross-section as in FIG. 5 showing a plurality of single-armed and double-armed sutures in the suture winding channel separated by spacer elements; the retaining door is shown in the closed position.

FIG. 7 is a perspective view of a surgical procedure kit of the present invention consisting of a package of the present invention containing a plurality of sutures (in a winding channel) and surgical needles (in a needle park means), wherein the package is contained in a sterile, sealed outer blister package.

FIG. 8 is a perspective view of a surgical procedure kit of the present invention consisting of two subkits each contained in a package of the present invention, each subkit containing a plurality of sutures and surgical needles, wherein both packages are contained in a sterile, sealed outer blister package.

FIG. 11 is a perspective view of a surgical procedure kit of the prior art consisting of a blister pack tray and a plurality of individually packaged sutures contained in plastic pockets.

DESCRIPTION OF THE PREFERRED EMBODIMENTS

Commonly assigned, co-pending U.S. patent application No. 901,356 filed on Jun. 19, 1992 is incorporated by reference.

Figure 1:
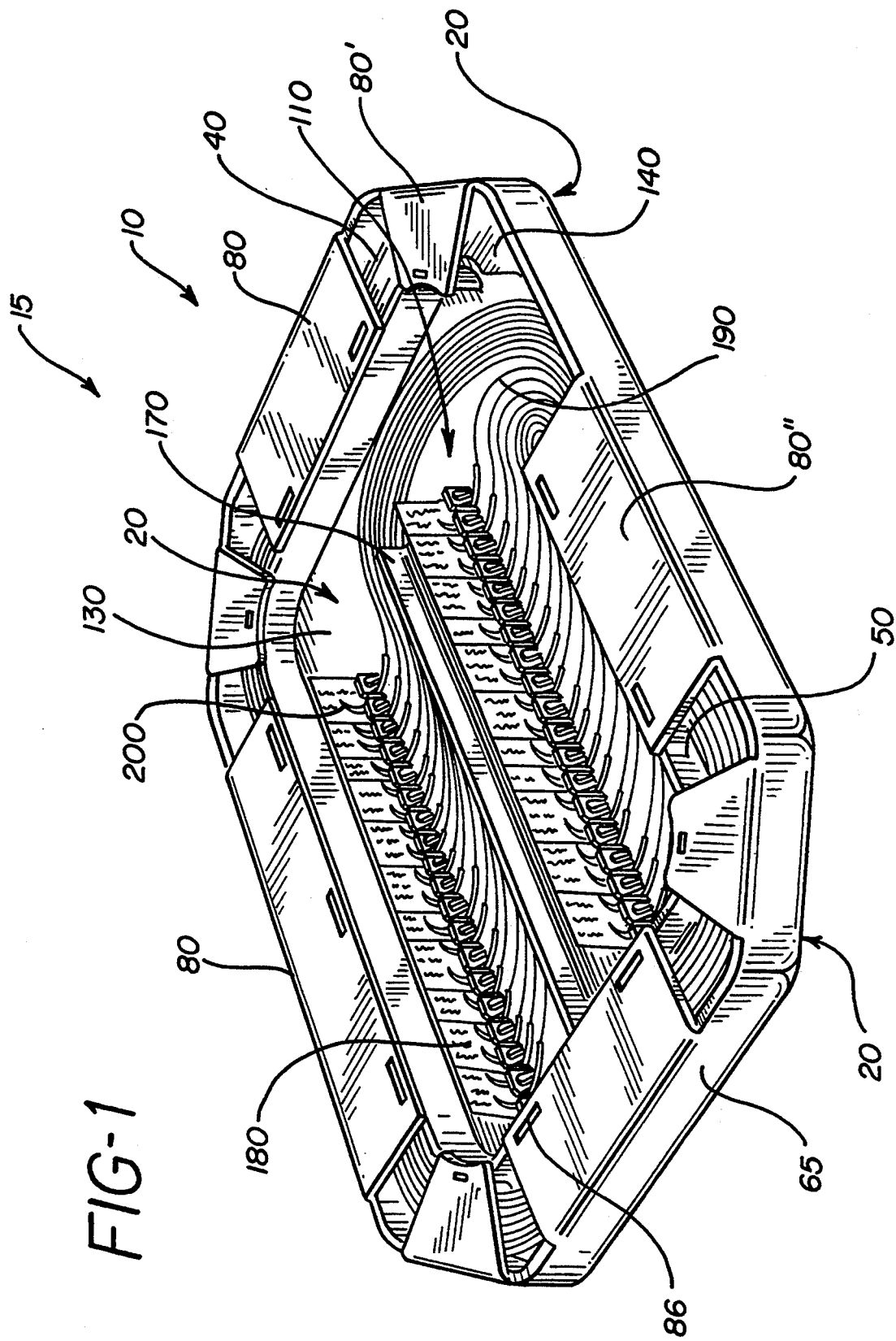
FIG. 1 is a perspective view of a surgical procedure kit and package of the present invention illustrating a package of the present invention containing a plurality of surgical needles and sutures, including single-armed and double-armed sutures.
Figure 2:
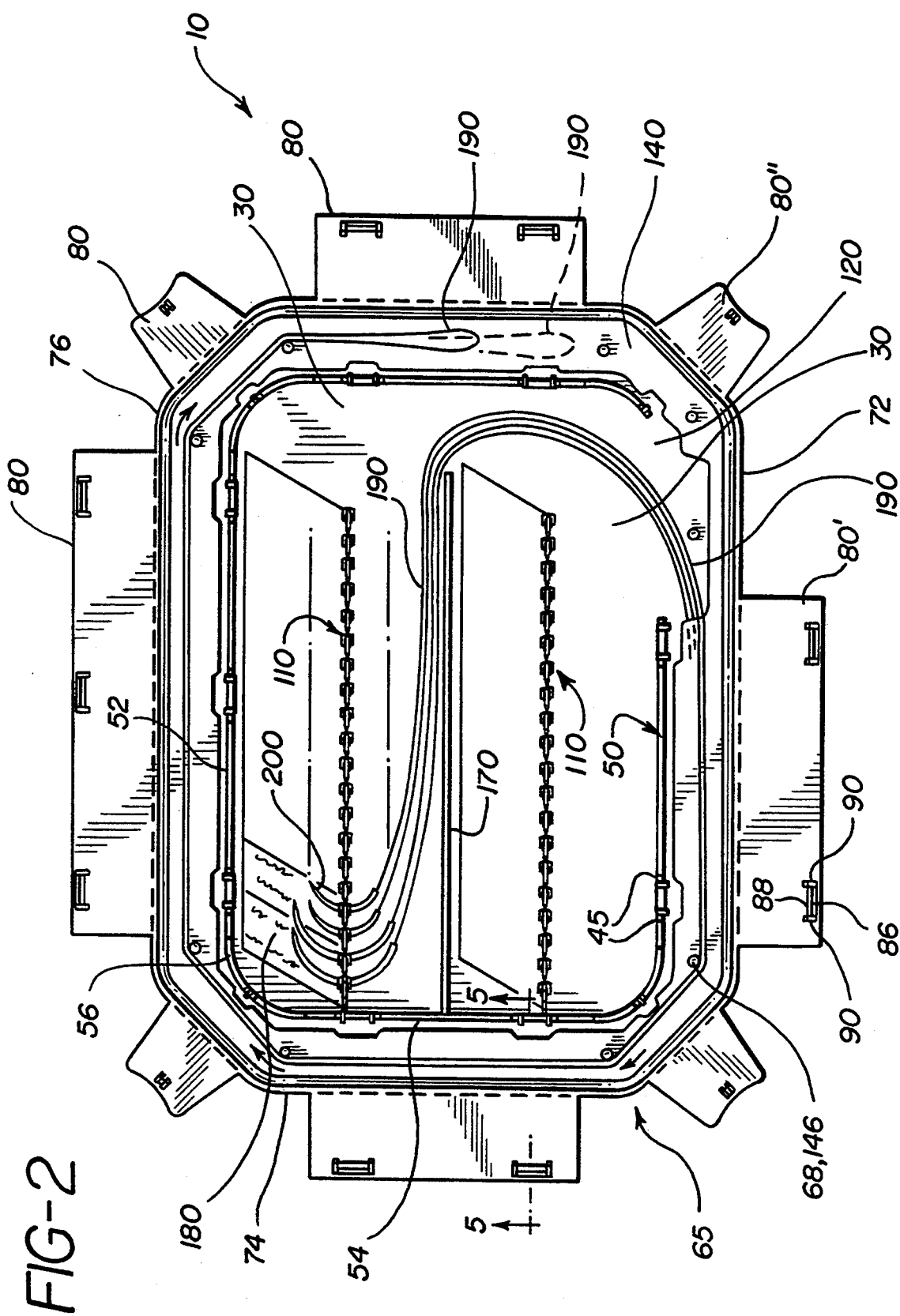
FIG. 2 is a plan view of the suture package of the present invention showing the spacer and double-armed sutures of FIG. 1A emplaced in the package.

A kit 15 of the present invention is seen in FIG. 1. Referring also to FIGS. 1, 1A and 2, a package 10 of the present invention is shown in perspective and plan views. Package 10 is seen to have a base 20 which has a central floor area 30. Central floor area 30 is surrounded by an outer channel suture 40. The channel 40 preferably has two opposed longitudinal sections and two opposed latitudinal sections. The terms longitudinal and latitudinal as used herein when referring to the package 10 are defined to mean substantially parallel to the major and minor axes, respectively, of the package 10. However, the channel 40 may have a variety of configurations including oval, square, rectangular, circular, polyhedral, etc.

The channel 40 is defined by an inner wall 50 which extends upwardly from the base 20 and the outer wall 65. The inner wall 50 surrounds the central floor area 30. The inner wall 30 may have a variety of configurations corresponding, generally, to the configuration of the channel 40, e.g., rectangular, oval, square, circular, polyhedral, etc. It is particularly preferred to have an inner wall consisting of longitudinal sections 52 and latitudinal sections 54. The longitudinal sections 52 of inner wall 50 and the latitudinal sections 54 of inner wall 50 are connected, preferably by optional curved sections 56. The curved sections 56 are seen to be extensions of walls 52 and 54 defining a curved shape, preferably, an arc of a circle. The sections 52 and 54 may be straight, or curved or combinations thereof. For example, sections 52 could be straight and sections 54 curved. When the sections 52 and/or 54 are curved, the chords of the curved sections will preferably be parallel to the longitudinal and latitudinal axes of the package 10. Portions of the door locking means are formed at intervals about the inner wall 50. As seen in FIG. 1A and FIG. 2, spacer members 140 are inserted into channel 40 in order to divide the channel 40 into coplanar sections. The spacer members 140 will be more fully described below.

Referring to FIG. 5 and FIG. 6, the bottom and outer periphery of the channel 40 are defined by bottom section 60 of the base 20 which extends outwardly preferably from the periphery of central floor area 30, and, by outer wall 65 which extends upwardly from the outer periphery 61 of bottom section 60. Outer curved section 62 is seen to connect the outer periphery 61 of bottom section 60 to the bottom of outer wall 65, however, periphery 61 may intersect the bottom of wall 65 at an angle, e.g., a right angle.

The outer wall 65 is similarly seen, preferably, to consist of a pair of opposed longitudinal walls 72, a pair of opposed outer latitudinal walls 74, and outer connecting walls 76. The outer connecting walls 76 may be shaped as shown or may have a curved or rounded configuration. The walls 72 and 74 may also intersect at an angle such as a right angle. However, the outer wall 65 will typically have a shape corresponding to the shape of the channel 40, e.g., circular, rectangular, oval, square, polyhedral, etc.

Referring to FIG. 1A, the spacer member 140 is seen to, preferably, be a substantially flat member having a central opening 141 bounded by a pair of opposed longitudinal sections 142 and a pair of opposed latitudinal sections 144. In a preferred embodiment, the spacer member 140 is seen to have end sections 145 which connect the ends of longitudinal sections 142 and latitudinal sections 144. The member 140 also has holes 146 extending therethrough and optional clearance cut-outs 147 in the inner sides of sections 144 and 142. The cutouts 147 correspond to the locations of standoffs 42 projecting out from wall 50 and serve to provide clearance. As mentioned previously, the spacer members 140 are inserted into channel 40 and serve to divide the channel 40 into coplanar sections. In order to package multiple double-armed sutures in the package 10, it is necessary to separate each double-armed suture from other double-armed and single-armed (or unarmed) sutures with the spacer members 140 in order to allow for easy release and removal. It should be noted that single-armed sutures or unarmed sutures do not have to be separated from each other with spacer members so that it is possible to have a kit 15 packaged in a package 10 consisting entirely of single-armed sutures (and/or unarmed) without any spacer members 140. However, it may be preferred to use spacer members 140 in such a kit 15, depending upon the types and sizes of sutures, to prevent tangling of the single-armed and/or unarmed sutures. Similarly, in a kit having double-armed sutures and single-armed sutures and/or unarmed sutures, it may be desirable to separate single-armed sutures with spacer members 140 as well as separating unarmed sutures with spacer members 140. It should also be noted that the spacer members 140 are not removed from the channel 40 when sutures are being removed from package 10. The spacer members 140 will have a configuration which will conform to the configuration of the channel 40 and may include configurations such as square, rectangular, oval, circular, polyhedral, etc. The spacer members 140 will be sized to effectively fit into the channel 40.

Attached at the top 67 of the outer wall 65 opposite to the inner wall 50, as can be seen in FIGS. 1, 2, 5 and 6, are the door means consisting of a plurality of hinged doors 80. FIG. 5 and FIG. 6 are partial cross-sectional views of the package 10 showing an enlargement of a door 80 hinged at hinge 83 to the top outer periphery 67 of the outer wall 65 of the channel 40 at an elevation which is preferably just below the uppermost elevation of the channel 40 so that the door 80 will preferably be substantially flush with the top of the channel 40 when it is closed. The hinge 83 is preferably a "living hinge". If one were willing to accept the disadvantages which may be attendant, if any, the doors 80 may be hinged from the inner wall 50.

Preferably, each door 80 has door locking means. The door locking means include a door latch opening 86 and a door latch projection 88. An overhang 89 is formed at the edge of the door 80. Fins 90 are located at each end of the door latch opening 86. It will also be noted that the doors 80 have upper surfaces 82. Preferably, the doors 80 are of sufficient length and are configured so that channel 40 is substantially or completely enclosed when the doors 80 are closed.

Referring concurrently to FIG. 2, FIG. 5 and FIG. 6, in a preferred embodiment, a latch post 41 is formed in the inner wall 50 opposite each door 80. A pair of standoffs 42 are formed along the inner wall 50 at either end of the latch post location. Extending from the latch post towards the inside of the package 10 (i.e., over the floor 30) is a latch post projection 46. When the door 80 is closed and latched to retain sutures within the channel 40, it has the cross-section as illustrated in FIG. 6. The top of the latch post 41 engages the door latch opening 86 and the door latch projection 88 hooks around latch post projection 46 to lock the door 80 in a closed position. The door 80 is prevented from unlatching in the presence of lateral compression by the abutment of the edge of the opening 86 against the edges of the standoffs 42, which inhibits unhooking of the two projections 46 and 88. When the door 80 is closed, the bottom of the door 80 adjacent to the opening 86 rests upon the edges 45, shown in FIG. 2, and the remainder of the door 80 adjacent to the edges 45 rests upon inner wall 50. The fins 90 at either end of the opening 26 engage the openings at either end of the latch post. The fins 90 and the standoffs serve to prevent the sutures from binding or become entrapped in the door locking means. As illustrated in FIG. 5 and FIG. 6, the fins 90 and the standoffs 42 cause the sutures to be located away from and to bridge the engaged door opening 86 and latch posts 42, thereby preventing sutures 190 from becoming caught between these two members, either during closure of the door 80 or during withdrawal of sutures 190 from the channel 40.

It will be appreciated by those skilled in the art that equivalent locking means may be used to lock doors 80 other than the locking means shown in FIGS. 2, 5, and 6. In an alternate embodiment (not shown), the door locking means may include a plurality of posts located around the outer surface of the wall 50 in alignment with the doors 80. The posts are offset from the surface of the wall 50 to provide standoffs for the suture from the wall 50. The door locking means also includes a pair of holes formed in each door 80. When the hinged doors 80 are closed, the posts mate in the holes of the doors 80 in a force fit to hold the doors 80 closed. The posts can alternatively be sized to extend through the doors 80, enabling the tips of the posts to be swaged to secure the doors 80 in their closed position.

Figure 10:
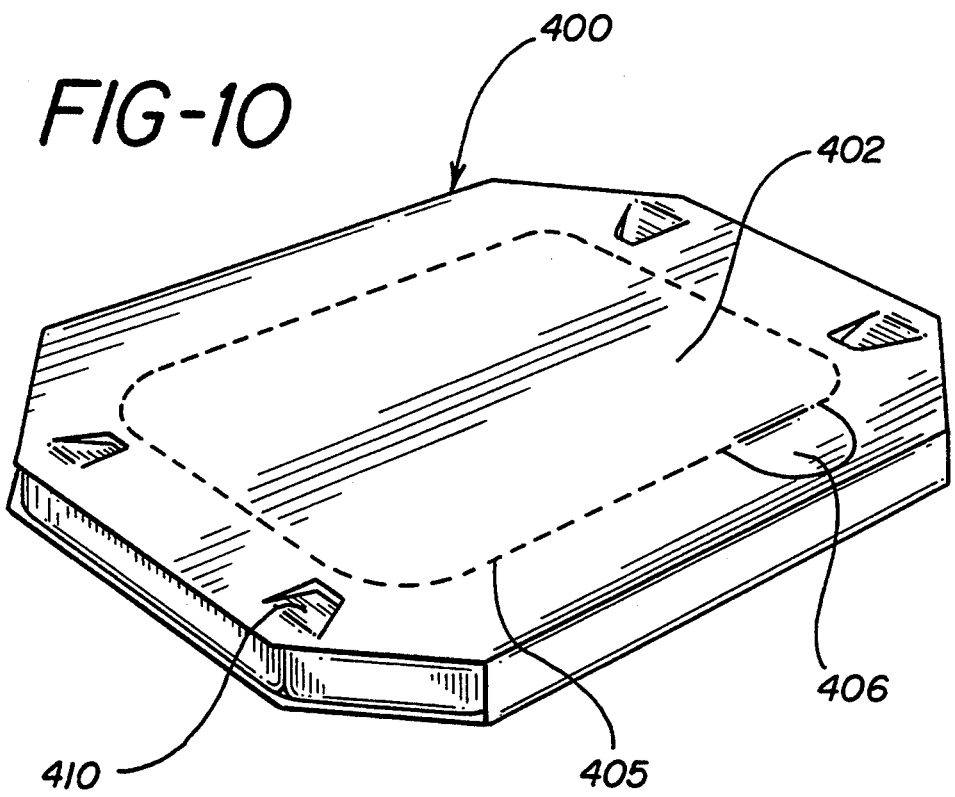
FIG. 10 is a perspective of the package of the present invention in an outer paper sleeve.

In yet another embodiment of the present invention, the doors 80 are eliminated. The package 10 may be enclosed in a paper sleeve 400 as seen in FIG. 10 or equivalents thereof. Alternatively, the channel 40 is enclosed, either wholly or partially, by a flat, paper cover having a plurality of holes about its periphery (not shown). Similarly, a plurality of posts extends upward from the top of inner wall 50. The posts are in alignment with the holes in the paper cover and are engaged by said holes. The ends of the posts which extend through the cover are then softened or swaged to hold the cover in place. The paper cover may further include cover flaps overlying the needle parks 110 of the package 10. The cover flap is hinged to the cover at a fold line.

As can be seen in FIG. 1, FIG. 2 and FIG. 3, located inside the outer channel 40 and extending from or mounted to the floor area 30 are a pair of needle parks 110 for holding needles 200. The needle parks 110 may comprise any conventional needle park means, including foam members, paper members and the like, wherein a plurality of needles 200 is held in a member having openings, slits or slots, etc., therein for receiving and holding the needles 200. Preferably, a portion of the inner wall 50 is eliminated in the vicinity of the needle park 110 to form a vent 120 in the inner wall 50 through which the sutures and the needles access channel 40 between the doors 80' and 80". It is also seen that the bottom section 60 of the outer channel 40 is periodically perforated by holes 68 (used in winding sutures 190) located around the periphery of the channel 40.

Referring to FIGS. 1, 2, 3, and 4, a preferred embodiment of a needle park 110 of the package 10 can be seen. It is particularly preferred to use a needle park means 110 comprising of plurality of members 115 extending from the base 20. The members 115 are seen to extend from the base 20 in inner area 30 to form at least one and preferably two needle parks 110 separated by longitudinal wall 170 which extends upwardly from base 20. The members 115 are separated from each other by gaps 116. A needle 200 is inserted into a gap 116 and is compressively retained by members 115. Members 115 extend from base 20 and have a "living-hinge" arrangement wherein they are capable of sufficient deflection to effectively accommodate a variety of needle widths and sizes in the gap 116. The leg 118 of member 115 is rotatable about hinge 117 into gap 119 thereby increasing the size of gap 116. Needle park means comprising members having a living hinge attachment to a base are described in commonly assigned, U.S. Pat. No. 5,131,533 which is incorporated by reference. The optional wall 170 is seen to extend from the base 20 and functions to separate adjoining needle parks 110. Typically the number of walls 170 present in a package 10 will be one less than the number of needle parks 110 so that adjacent needle parks 110 are separated by at least one wall 170. The height of wall 170 will typically be less than or equal to the height of inner wall 50. It is preferred to have at least one wall 170 in package 10 when more than one needle park is present in order to protect sutures in adjoining needle parks 110 against damage from needle points when needles are removed from the needle parks 110. Although not shown, a slit may be formed in the base 20 adjacent to each needle park 110 to form a moveable flap which may be deflected downward when a conventional needle holder is used to grasp a needle 200 in needle park 110, thereby facilitating grasping and removal of the needle 200 with the needle holder.

Located adjacent to each needle park 110 are labels 180 which identify each needle 200 and suture 190. Labels 180 may be conventional printed labels or equivalents thereof which are mounted to inner area 30 with conventional adhesives or bonding agents. If desired, labels 180 may be printed directly upon inner area 30. The labels will preferably identify each needle 200 and suture 190 with regard to various parameters and characteristics including, inter alia, type, size, length, absorbable/non-absorbable, etc. In addition color codes may be utilized in the labels 180 for quick identification of needles 200 and sutures 190.

The package 10 of the present invention may be formed of any surgically compatible polymeric material such as polyester plastic, polyethylene, polyvinyl chloride (PVC), polypropylene, polystyrene and combinations thereof and the like. If desired, a sufficient amount of at least one conventional lubricating material may be added to the polymeric material effective to provide decreased frictional resistance to the withdrawal of a suture from the package 10. Conventional lubricants include oleamides, organosilicones and the like.

The polymeric package 10 can be tinted or colored a milky white or some other contrasting color, using conventional dyes or pigments approved for medical use, which will highlight the needle in front of the floor area 30. A contrasting background may make it easier to clearly see fine gauge needles 200 in the package 10.

The separator members 140 may be made from any surgically compatible material having the requisite mechanical properties, in particular, rigidity and stiffness. The materials include paper, polymeric materials, metals and laminates thereof. The polymeric materials include polyethylene, PETG, proprionate(CAP), and polypropylene. The thickness of spacer member 140 will be sufficient to provide effective stiffness and will vary with the type of material utilized. The members 140 are made using conventional cutting processes including die cutting and the like, and may also be molded using conventional molding processes and equipment.

Referring to FIG. 1 and FIG. 7, a kit 15 of the present invention comprising an assembled package 10 with needles 200 and sutures 190 is shown. The kit 15 is easily assembled in package 10 by placing the package 10 on a conventional assembly platform with a number of upwardly extending pins. A plurality of pins extend upward and are aligned to pass through the holes 68 of the channel 40 (see FIG. 2) and through holes 146 of spacer members 140. The assembly platform is open beneath the channel holes 68 and a vacuum source below the platform draws air through the holes 68 and 146. With the package 10 so emplaced, the needles 200 are located in the needle park 110 as shown in FIGS. 1, 2, 6 and 7 and the sutures 190 are looped about the pin extending through hole 69 then downward through the vent 120 and into the channel 40. The sutures 190 are then wound, preferably in a clockwise direction, around the pins which extend through the channel holes 68 and the spacer members 140. Double-armed sutures are preferably wound by emplacing both needles 200 in the needle park 110 adjacent to each other, and then winding the resulting double strand suture loop in a clockwise manner in channel 40. However, double-armed sutures may also be wound by emplacing a first needle in the needle park 110 and then winding one-half of the suture 190 clockwise in channel 40 and then looping the remainder of the suture 190 back in a counterclockwise direction and emplacing the second needle in the needle park 110 adjacent to the first needle. As mentioned previously herein, each double-armed suture 190 must be separated from other single-armed, unarmed and double-armed sutures 190 by spacer members 140 which are placed into channel 40 and over the winding pins which are inserted into holes 146. In a preferred method, the single armed sutures 190 are either wound prior to or after winding the double-armed sutures 190 and will therefore be located at the bottom or at the top of the channel 40 on top of a spacer 140 (see FIG. 6). It is also possible to wind unarmed sutures in the channel 40 of package 10. One end of an unarmed suture 190 will be placed in needle park 110. When the sutures 190 are wound around the pins and the pins then are withdrawn from the holes 68 and 146, the sutures 190 will be loosely positioned, preferably, approximately in the center of channel 40, since the pins also serve to locate the sutures 190 away from the inner wall 50 in the channel 40 during winding. As the sutures 190 are wound around the pins, the flow of air through the holes 68 and 146 will draw the sutures 190 down into the channel 40. When the end, or "tail" of each suture is reached, the flow of air will likewise draw the tail of the suture 190 into the channel 40.

As mentioned above, each double-armed suture 190 will be separated from other sutures 190 in the channel 40 by a spacer member 140. A spacer member 140 will typically be placed in channel 40 in a coplanar manner below and above each double-armed suture 190. Although, if a double-armed suture 190 is the first suture wound in the channel 40, there is no need for a spacer member 140 below the suture 190. Each double-armed suture 190 will be wound in a slightly different manner from single-armed sutures 190 as can be seen in FIGS. 1A and 2. Both needles 200 of a double armed suture 190 are typically placed into needle park 110 in adjoining spaces 116 prior to winding the suture 190, however as previously mentioned, an alternate method may be used. Then, typically, the double-armed suture 190 is wound on top of a spacer member 140. Then another spacer member 140 is placed into channel 140 on top of the double-armed suture 190.

When the sutures 190 are completely wound in the channel 40, the doors 80 are closed and latched to the latch posts 41 of the inner wall 50. The pins are then withdrawn from the holes 68 and 146.

Referring to FIG. 10, an optional paper cover 400, which may comprise a sleeve-like member, may be placed about the package 10 and kit 15 to, inter alia, fully protect the sutures and needles from any further contact during final assembly of the package 10. The optional cover may include a scored tear line 405 along which the top 402 of cover 400 which will preferentially tear when it is grasped at a tab 406 for opening, thereby exposing the inner area 30. Tabs 410 are seen to engage the package 10. In an alternate embodiment (not shown) the cover may comprise a flat member having a plurality of perforated push-out tabs. These tabs are located so as to be in alignment with the closed doors. When the tabs are pressed downward, the outer edges of the tabs snap under the overhanging edges of the doors with which they are aligned, thereby retaining the cover in place on the package 10.

Figure 9:
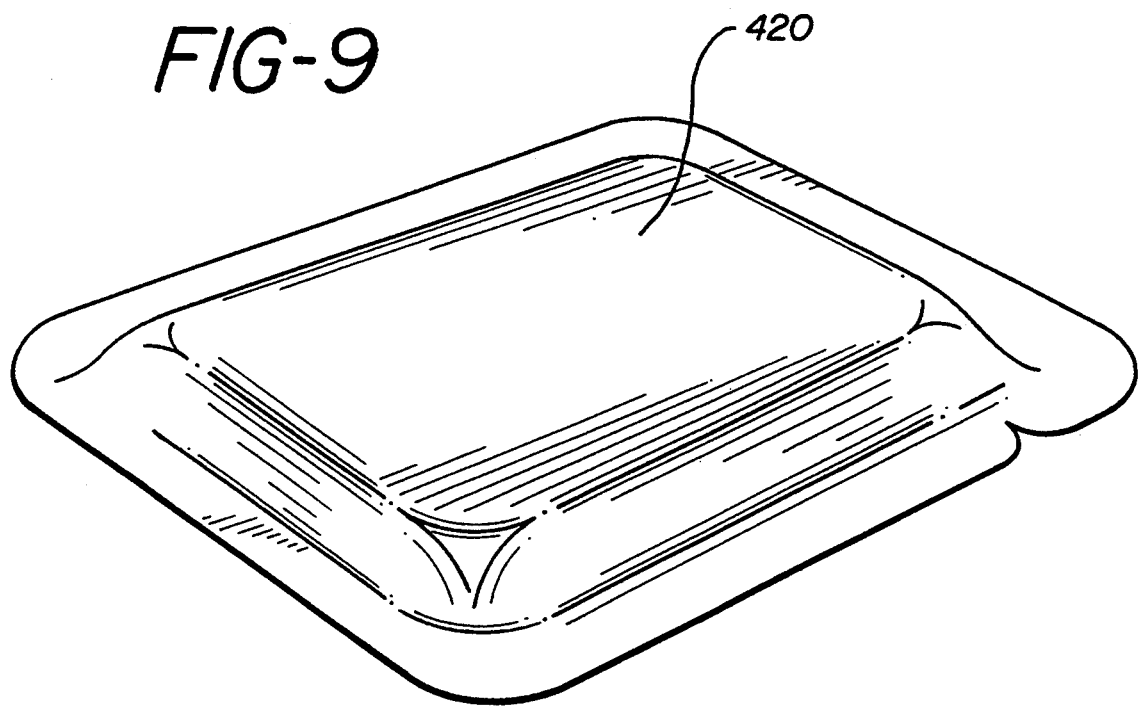
FIG. 9 is a perspective view of a kit of the present invention in a conventional foil overwrap.

When using certain types of sutures, in particular, certain absorbable sutures such as catgut, the kit 15 (including package 10) is preferably placed into a conventional foil wrap package 420 (as seen in FIG. 9) which is then sealed in a conventional manner.

The kit 15, containing surgical sutures 190 and needles 200 in package 10, is then ready for final overwrap packaging, which typically comprises hermetically sealing the kit 15 package in a conventional plastic blister package 500 having a peelable cover 505 as seen in FIG. 7 using conventional sealing and packaging techniques. Next, the sealed kit is sterilized using conventional sterilization techniques including autoclaving, radiation sterilization using cobalt-60, and the like.

In the package 10 of the present invention, it can be seen that the suture 190 is looped to the right from the barrel of needle 200 through the vent 120. This winding pattern keeps the suture 190 removed to the right of the needle 200 and the needle point 201. As the needle 200 is lifted from the needle park 110 and the suture 190 is pulled from the channel 40, the suture 190 is kept to the right of and away from the point 201 of the needle 200 and any possible damage. The longitudinal wall 170 between the needle parks 110 also serves to prevent needles 200, as they are being removed from a needle park 110, from damaging sutures 190 extending from needles 200 in an adjacent needle park 110.

The packages 10 and kits 15 of the present invention have many advantages over the kit packages and kits of the prior art. Surprisingly and unexpectedly, the packages 10 of the present invention allow the sutures 190 and needles 200 required for an entire surgical procedure, consisting of single- and double-armed sutures 190 (and unarmed sutures if required) of various types and sizes and lengths, to be collectively packaged in a single package 10 to form a procedure kit 15. Certain surgical procedures may require more than one package 10 for a kit 15 because of the large quantity of needles needed to perform the procedure. In such a case, several subkits 16 are provided to form kit 15, each subkit consisting of a plurality of needles and sutures packaged in a package 10.

Referring to FIG. 11, a procedure kit 300 of the prior art is illustrated. The kit 300 consists of a blister pack tray 310 containing a plurality of plastic wallets 320 having plastic pockets 325 formed therein. Each plastic packet 325 contains a suture package 330 which in turn contains an armed or unarmed suture 340. A plurality of the wallets 320 are typically fastened together. In utilizing the kit 300 in the operating theater, the scrub nurse initially opens the peel away top 315 of the blister pack tray 310. Then the wallets 320 must be removed from the blister pack 310. Next each needle package 330 must be removed from the pockets 325, and, each package 330 must be opened and the needle 345 and suture 340 removed by the scrub nurse. Not only is this procedure time consuming, it can be appreciated that the amount of packaging waste generated by the use of such a kit is substantial. In addition, because of the large quantity of individually packaged sutures, it may be difficult for the scrub nurse to locate or account for particular needles 345 or sutures 340. A significant effort must be made to collect and dispose of such packaging waste. In contrast, when using the kit 15 and package 10 of the present invention, the scrub nurse removes the kit from a blister package 500. If a paper cover 400 or foil wrap 400 is present it is removed. The sutures 190 and needles 200 for the surgical procedure are then visible, identified, and available for immediate use without the need for opening individual suture packages. Also, the package 10 provides a means for accurately accounting for the disposition of all needles 200 and sutures 190 in the kit by visually scanning the inner area 30 of each package 10.

It will be appreciated by those skilled in the art that a surgical procedure typically requires both absorbable and nonabsorbable sutures. Nonabsorbable sutures typically would not be mixed with absorbable sutures in the packages 10 of kits 15 (although this could be done if one were willing to accept the disadvantages that might be attendant, if any). For example, absorbable cat-gut sutures could not be mixed with nonabsorbable sutures. Accordingly, the kit 15 may then consist of a sub-kit 16 of armed and/or unarmed) absorbable sutures 190 in a first package 10 and a sub-kit 16 of armed (and/or unarmed) nonabsorbable sutures 190 in a second package 10. However, it is possible to package absorbable sutures 190 and nonabsorbable sutures 190 (other than cat-gut) in the same package 10 to form a kit 15.

In addition, it will be further appreciated that the number of sutures 190 and needles 200 for a particular procedure may be too numerous to package in a single package 10. In such a case two or more packages 10 would be used to package the sutures 190 and needles 200 to form a kit 15. For example, a kit 15 is seen in FIG. 8 having two sub-kits 16 packaged in a single blister package 500. It will be appreciated by one skilled in the art that the dimensions of the blister package 500 are changed to accommodate the kit 15 configuration when sub-kits 16 are present. In addition, as previously mentioned, it is possible to have a kit 15 consisting of a sub-kit 16 of nonabsorbable armed sutures and another sub-kit 16 of absorbable sutures.

The sutures 190 and needles 200 which can be packaged in the packages 10 to form the kits 15 include conventional armed and unarmed sutures and surgical needles of various types, materials, sizes and lengths. If desired, it is possible to have a kit 15 comprising only single-armed (and/or unarmed) sutures of various sizes, types and lengths. The needles 200 and sutures 190 would be packaged in at least one package 10 as previously described, however the spacer member 190 would be optional in the channel 40 since no double-armed sutures would be present.

Various sizes and types of conventional sutures 190 and equivalents thereof may be packaged in the kits 15 and subkits 16 of the present invention. The sutures 190 may include monofilament, braided, nonabsorbable, and absorbable sutures and the like. Examples of sutures which may be used include Prolene ® (polypropylene), nylon and silk sutures as well as Vicryl ® and catgut sutures available from ETHICON, Inc., Somerville, New Jersey. The needles 200 may include conventional needles including straight, curved and combination curved and straight needles having taper points, cutting points and round points, and equivalents thereof. The needles may vary according to length, needle size, diameter, material of construction, etc. Such needles are also available from ETHICON, Inc.

The kits 15 of the present invention will contain all or substantially all of the surgical needles and sutures, both armed and unarmed, absorbable and nonabsorbable needed for a surgical procedure. The procedures include all conventional procedures including cardiovascular, gynecological, obstetrical, orthopedic, ophthalmic, gastro-intestinal, pulmonary, etc.

The following Example is illustrative of the principles and practice of the present invention although not limited thereto.

EXAMPLE

A procedure kit 15 for a cardiovascular surgical procedure is assembled in a package 10. The kit 15 contains the sutures 190 and needles 200 listed in the Table. The kit 15 is assembled by mounting the package 10 onto a conventional winding apparatus having pins which are inserted through holes 68. The needles 200 for each single-armed or double armed suture 190 are placed into spaces 116 of needle parks 110. In addition, one end of each unarmed suture 190 is placed into a space 116 of needle park 110. The sutures are then wound about the pins into channel 40. Spacer members 140 are placed between each double-armed suture 190 and other single-armed or double-armed sutures 190 by placing the members 140 into channel 40 over the winding pins such that the pins are inserted through the holes. The doors 80 are closed over channel 40 after the sutures 190 and needles 200 have been placed in package 10. The kit 15 is then placed into an optional paper sleeve 400 and placed into a conventional blister pack 500 having a sealed cover 520. The kit is then effectively sterilized using conventional sterilization techniques.

The suture packages 10 and kits 15 of the present invention have many advantages over the kit packages and kits of the prior art. Surprisingly and unexpectedly, it is now possible to package numerous types and sizes and lengths of surgical needles and sutures in a single package, including single-armed, unarmed and double-armed sutures, as well as absorbable and nonabsorbable sutures. It is believed that this was not previously possible. The efficiency of the scrub nurse in opening a package 10 and removing needles 200 and sutures 190 from a kit 15 is greatly improved when compared to the kits of the prior art containing individually packaged needles and sutures. In addition, substantial amounts of packaging are no longer needed since all of the needles 200 and sutures 190 needed for the surgical procedure are packaged into a single package (or several packages 10 if kit 15 has subkits 16). In addition, the needles 200 and sutures 190 are readily identified, both visually and by labeling, in the suture package 10 and easily removed. The sutures 190 and needles 200 are further available for immediate use.

Further, each needle 200 and suture 190 is readily accounted for during the surgical procedure.

Although this invention has been shown and described with respect to detail embodiments thereof, it will be understood by those skilled in the art that various changes and form and detail thereof maybe made without the departing from the spirit and scope of the claim invention.

What is claimed is:

1. A package for a surgical suture and needle procedure kit that defines a suture winding channel, comprising:
   a base having a central area, the central area having an outer periphery;
   an inner wall extending up from the base about the central area wherein the inner wall comprises a pair of substantially opposed inner longitudinal walls extending from the base and, a pair of substantially opposed inner latitudinal walls extending from said base, said latitudinal walls being connected to said longitudinal walls wherein the inner longitudinal walls and the inner latitudinal walls are connected by curved intermediate walls sections;
   an outer wall extending up from the base, wherein the inner wall and the outer wall form a suture winding channel;
   at least one spacer means located in the channel for separating the channel into at least two coplanar sections;
   a plurality of door means hingingly attached to the suture winding channel, the door means being closable to enclose a suture within the suture winding channel; and,
   means for locking said door means in their closed position.

2. The package of claim 1 wherein said package further comprises a point of access to the central area from said suture winding channel and wherein said point of access allows passage of a suture from said central area into said channel.

3. The package of claim 2, wherein said point of access comprises an opening in the inner wall of said suture winding channel.

4. The package of claim 1, further comprising at least one means for parking at least one needle located in said central area.

5. The suture package of claim 4 comprising more than one means for parking at least one needle.

6. The package of claim 5 comprising at least one longitudinal wall extending from the base between adjacent means for parking at least one needle.

7. The package of claim 6 comprising two means for parking at least one needle.

8. The package of claim 4 wherein the means for parking at least needle comprises a plurality of hinged members extending from the base, said hinged members located along a longitudinal line.

9. The package of claim 1, comprising a point of access located in the vicinity of the connection of a longitudinal section to a latitudinal section.

10. The package of claim 1, wherein said suture winding channel comprises an open side, and said door means are hingingly attached at said open side of said channel for closure over said open side of said channel.

11. The package of claim 10, wherein said channel further comprises standoff means projecting from an inner wall of said channel for bridging sections of said inner wall.

12. The package of claim 1, wherein said locking means comprise a latch mechanism located on said door means and said channel.

13. The package of claim 12 wherein said latch mechanism further comprises an aperture located in said door means and an interlocking post located on said channel.

14. The package of claim 13, wherein said door means further comprises fin means projecting from said door means for preventing binding of a suture within said latch mechanism.

15. The package of claim 1, wherein said suture winding channel is located about the periphery of the central area.

16. The package of claim 1, wherein said suture winding channel in at least one cross-section comprises a substantially planar inner wall, a planar top wall formed by said door means, a substantially planar outer wall and a substantially planar bottom wall connecting said inner and outer walls, when said door means are closed.

17. The suture package of claim 1 further comprising a cover sleeve enclosing said package.

18. The package of claim 1 further comprising means for labeling located on the central area for identifying each needle and suture.

19. The package of claim 1 wherein each spacer means comprises planar member inserted into the channel, said member having a central hole therethrough such that the member fits in the winding channel.

20. A package for a surgical suture and needle procedure kit that defines a suture winding channel, comprising:
   a base having a central area, the central area having an outer periphery;
   an inner wall extending up from the base about the central area said inner wall comprising a pair of substantially opposed inner longitudinal walls extending from the base and a pair of substantially opposed inner latitudinal walls extending from said base, said latitudinal walls being connected to said longitudinal walls;
   an outer wall extending up from the base, wherein the inner wall and the outer wall form a suture winding channel wherein the inner longitudinal walls and the inner latitudinal walls are connected by curved intermediate walls sections;
   a plurality of door means hingingly attached to the suture winding channel, the door means being closable to enclose a suture within the suture winding channel and means for locking said door means in their closed position;
   at least one spacer means located in the channel for separating the channel into at least two coplanar sections; and,
   at least one needle park means located in said central area.

21. The package of claim 20, wherein said package further comprises a point of access to the central area from said suture winding channel and wherein said point of access allows passage of a suture from said central area into said channel.

22. The package of claim 21, wherein said point of access comprises an opening in the inner wall of said suture winding channel.

23. The package of claim 20, comprising a point of access located in the vicinity of the connection of a longitudinal section to a latitudinal section.

24. The package of claim 20, wherein winding area of said package, said suture winding channel comprises an open side, and said door means are hingingly attached at said open side of said channel for closure over said open side of said channel.

25. The package of claim 24, wherein said channel further comprises standoff means projecting from an inner wall of said channel for bridging sections of said inner wall.

26. The package of claims 24, wherein said locking means comprises a latch mechanism located on said door means and said channel.

27. The package of claim 26 wherein said latch mechanism comprises an aperture located in said door means and in interlocking post located on said channel.

28. The package of claim 27, wherein said door means further comprise fin means projecting from said door means for preventing binding of a suture within said latch mechanism.

29. The package of claim 20, wherein said suture winding channel is located about the periphery of said package and includes an inner wall projecting from the floor of said package.

30. The package of claim 20, wherein said suture winding channel in at least one cross-section comprises a substantially planar inner wall, a planar top wall formed by said door means, a substantially planar outer wall and a substantially planar bottom wall connecting said inner and outer walls, when said door means are closed.

31. The suture package of claim 20 further comprising a cover sleeve enclosing said package.

32. The suture package of claim 20 comprising more than means for parking at least one needle.

33. The package of claim 32 comprising at least one longitudinal wall extending from the base between adjacent means for parking at least one needle.

34. The package of claim 33 comprising two means for parking at least one needle.

35. The package of claim 20 wherein the means for parking at least one needle comprises a plurality of hinged members extending from the base located along a longitudinal line.

36. The package of claim 20 further comprising means for labeling located on the central area for identifying each needle and suture.

37. The package of claim 20 wherein the spacer means comprises at least one planar member inserted into the channel, the member having a central hole therethrough such that the member fits in the winding channel.

38. The package of claim 20 further comprising a foil overwrap in which the package is sealed.

39. The package of claim 20 further comprising a paper sleeve in which the package is contained.

40. The package of claim 20 further comprising an outer blister package in which the package is sealed.

41. The package of claim 20 additionally comprising at least two surgical sutures and at least two surgical needles, wherein at least one suture is a double-armed suture.

42. A surgical suture and needle procedure kit, comprising:
- I) a package for surgical needles and sutures that defines a suture winding channel, said package comprising:
  - a base having a central area, the central area having an outer periphery;
  - an inner wall extending up from the base about the central area;
  - an outer wall extending up from the base, wherein the inner wall and the outer wall form a suture winding channel; and,
  - at least one spacer means located in the channel for separating the channel into at least two coplanar sections; and
- II) at least two surgical needles and at least two surgical sutures, the needles placed in the central area and the sutures wound in the suture winding channel, wherein at least one of the sutures in a double-armed suture.

43. The package of claim 42 wherein the inner wall comprises:
- a pair of substantially opposed inner longitudinal walls extending from the base; and,
- a pair of substantially opposed inner latitudinal walls extending from said base, said latitudinal walls being connected to said longitudinal walls.

44. The kit of claim 43 wherein the inner longitudinal walls and the inner latitudinal walls are connected by curved intermediate walls sections.

45. The package of claim 43 comprising a point of access is located in the vicinity of the connection of a longitudinal section to a latitudinal section.

46. The kit of claim 42 further comprising a plurality of door means hingingly attached to the suture winding channel, the door means being closable to enclose a suture within the suture winding channel.

47. The kit of claim 46 further comprising means for locking said door means in their closed position.

48. The kit of claim 47, wherein said locking means comprises a latch mechanism located on said door means and said channel.

49. The kit of claim 48 wherein said latch mechanism further comprises includes an aperture located in said door means and an interlocking post located on said channel.

50. The kit of claim 49, wherein said door means further comprises fin means projecting from said door means for preventing binding of a suture within said latch mechanism.

51. The kit of claim 46, wherein said suture winding channel has an open side, and said door means are hingingly attached at said open side of said channel for closure over said open side of said channel.

52. The kit of claim 51, wherein said channel further includes standoff means projecting from an inner wall of said channel for bridging sections of said inner wall.

53. The kit of claim 46, wherein said suture winding channel in at least one cross-section comprises a substantially planar inner wall, a planar top wall formed by said door means, a substantially planar outer wall and a substantially planar bottom wall connecting said inner and outer walls, when said door means are closed.

54. The kit of claim 42, wherein said package further comprises a point of access to the central area from said suture winding channel and wherein said point of access allows passage of a suture from said central area into said channel.

55. The kit of claim 54, wherein said point of access comprises an opening in an inner wall of said suture winding channel.

56. The kit of claim 42, further comprising at least one means for parking at least one needle located in said central area.

57. The kit of claim 56 comprising more than one means for parking at least one needle.

58. The kit of claim 57 comprising at least one longitudinal wall extending from the base between adjacent means for parking at least one needle.

59. The kit of claim 58 comprising two means for parking at least one needle.

60. The kit of claim 42, wherein said suture winding channel is located about the periphery of the central area.

61. The kit of claim 42 further comprising a cover sleeve enclosing said package.

62. The kit of claim 42 wherein the means for parking at least one needle comprises a plurality of hinged members extending from the base, said hinged members located along a longitudinal line.

63. The kit of claim 42 further comprising means for labeling located on the central area for identifying each needle and suture.

64. The package of claim 42 wherein the spacer means comprises at least one planar member inserted into the channel, the member having a central hole therethrough such that the member fits in the winding channel.

65. The kit of claim 42 further comprising a foil overwrap in which the kit is sealed.

66. The kit of claim 42 further comprising a paper sleeve in which the kit is enclosed.

67. The kit of claim 42 further comprising a paper cover for covering the kit.

68. The kit of claim 42 further comprising an outer blister package in which the kit is sealed.

69. The kit of claim 42 comprising at least one additional package for the surgical sutures and needles.

70. The kit of claim 69 further comprising an outer plastic blister package in which the kit is sealed.

71. The kit of claim 42 wherein the sutures comprise absorbable sutures.

72. The kit of claim 42 wherein the sutures comprise nonabsorbable sutures.

73. A surgical suture and needle procedure kit, comprising:
- I) a package for surgical needles and sutures that defines a suture winding channel, said package comprising:
  - a base having a central area, the central area having an outer periphery;
  - an inner wall extending up from the base about central area;
  - an outer wall extending up from the base, wherein the inner wall and the outer wall form a suture winding channel;
  - at least one spacer means located in the channel for separating the channel into at least two coplanar sections; and,
  - at least one means for parking at least one needle located in said central area; and,
- II) at least two surgical needles and at least two surgical sutures, the needles engaged by the needle park means and the sutures wound in the suture winding channel, wherein at least one of the sutures is a double-armed suture.

74. The kit of claim 73 wherein the inner wall comprises
a pair of substantially opposed inner longitudinal walls extending from the base; and,
a pair of substantially opposed inner latitudinal walls extending from said base, said latitudinal walls being connected to said longitudinal walls.

75. The kit of claim 74 wherein the inner longitudinal walls and the inner latitudinal walls are connected by curved intermediate walls sections.

76. The kit of claim 74 comprising a point of access is located in the vicinity of the connection of a longitudinal section to a latitudinal section.

77. The kit of claim 73 further comprising a plurality of door means hingingly attached to the suture winding channel, the door means being closable to enclose a suture within the suture winding channel.

78. The kit of claim 77 further comprising means for locking said door means in their closed position.

79. The kit of claim 78, wherein said locking means comprises a latch mechanism located on said door means and said channel.

80. The kit of claim 79 wherein said latch mechanism further comprises an aperture located in said door means and in interlocking post located on said channel.

81. The kit of claim 80, wherein said door means further includes fin means projecting from said door means for preventing binding of a suture within said latch mechanism.

82. The kit of claim 77, wherein said suture winding channel is located about the periphery of a central area of said package, said suture winding channel has an open side, and said door means are hingingly attached at said open side of said channel for closure over said open side of said channel.

83. The kit of claim 82, wherein said channel further includes standoff means projecting from an inner wall of said channel for bridging sections of said inner wall.

84. The kit of claim 77, wherein said suture winding channel in at least one cross-section comprises a substantially planar inner wall, a planar top wall formed by said door means, a substantially planar outer wall and a substantially planar bottom wall connecting said inner and outer walls, when said door means are closed.

85. The kit of claim 73, wherein said package further comprises a point of access to the central area from said suture winding channel and wherein said point of access allows passage of a suture from said central area into said channel.

86. The kit of claim 85, wherein said point of access comprises an opening in the inner wall of said suture winding channel.

87. The kit of claim 73, wherein said suture winding channel is located about the periphery of the central area.

88. The kit of claim 73 further comprising a cover sleeve enclosing said package.

89. The kit of claim 73 comprising more than one means for parking at least one needle.

90. The kit of claim 89 comprising at least one longitudinal wall extending from the base between adjacent means for parking at least one needle.

91. The kit of claim 90 comprising two means for parking at least one needle.

92. The kit of claim 73 wherein the means for parking a needle comprises a plurality of hinged members extending from the base located along a longitudinal line.

93. The kit of claim 73 further comprising means for labeling located on the central area for identifying each needle and suture.

94. The kit of claim 73 wherein the spacer means comprises at least one planar member inserted into the channel, the member having a central hole therethrough such that the member fits in the winding channel.

95. The kit of claim 73 further comprising a foil overwrap in which the kit is sealed.

96. The kit of claim 73 further comprising at least one additional package for the surgical sutures and needles.

97. The kit of claim 73 further comprising an outer blister package in which the kit is sealed.

98. The kit of claim 73 wherein the sutures comprise absorbable sutures.

99. The kit of claim 73, wherein the sutures comprise nonabsorbable sutures.

100. A surgical suture and needle procedure kit, comprising:
I) a package for surgical needles and sutures that defines a suture winding channel, said package comprising:
a base having a central area, the central area having an outer periphery;
an inner wall extending up from the base about central area;
an outer wall extending up from the base, wherein the inner wall and the outer wall form a suture winding channel;
at least one spacer means located in the channel for separating the channel into at least two coplanar sections; and,
at least one means for parking at least one needle located in said central area; and,
II) a plurality of surgical needles and sutures for a surgical procedure, the needles engaged by the needle park means and the sutures wound in the suture winding channel.

101. The kit of claim 100 further comprising a cover sleeve enclosing said package.

102. The kit of claim 100 comprising more than park means for parking at least one needle.

103. The kit of claim 102 comprising at least one longitudinal wall extending from the base between adjacent means for parking at least one needle.

104. The kit of claim 103 comprising two means for parking at least one needle.

105. The kit of claim 100 wherein the means for parking a needle comprises a plurality of hinged members extending from the base located along a longitudinal line.

106. The kit of Claim 100 further comprising means for labeling located on the central area for identifying each needle and suture.

107. The kit of claim 100 wherein the spacer means comprises at least one planar member inserted into the channel, the member having a central hole therethrough such that the member fits in the winding channel.

108. The kit of claim 100 further comprising a foil overwrap in which the kit is sealed.

109. The kit of claim 100 further comprising a paper sleeve in which the kit is sealed.

110. The kit of claim 100 further comprising an outer blister package in which the kit is sealed.

111. The kit of claim 100 wherein the sutures comprise absorbable sutures.

112. The kit of claim 100, wherein the sutures comprise nonabsorbable sutures.

113. The kit of claim 100 wherein the surgical sutures wound in the suture winding channel are single-armed sutures comprising a single needle mounted thereto and wherein the needles mounted to said single-armed sutures are engaged by the needle park means.

* * * * *